(12) United States Patent
Ueki

(10) Patent No.: US 12,076,528 B2
(45) Date of Patent: Sep. 3, 2024

(54) INJECTION SYSTEM, SYRINGE, AND GASKET

(71) Applicant: Circulus Inc., Tokyo (JP)

(72) Inventor: Jun Ueki, Yokohama (JP)

(73) Assignee: Circulus Inc., Tokyo (JP)

(*) Notice: Subject to any disclaimer, the term of this patent is extended or adjusted under 35 U.S.C. 154(b) by 781 days.

(21) Appl. No.: 17/274,729

(22) PCT Filed: Sep. 10, 2019

(86) PCT No.: PCT/JP2019/035546
§ 371 (c)(1),
(2) Date: Mar. 9, 2021

(87) PCT Pub. No.: WO2020/054715
PCT Pub. Date: Mar. 19, 2020

(65) Prior Publication Data
US 2021/0346599 A1 Nov. 11, 2021

(30) Foreign Application Priority Data
Sep. 13, 2018 (JP) ................. 2018-171532

(51) Int. Cl.
*A61M 5/145* (2006.01)
*A61M 5/315* (2006.01)

(52) U.S. Cl.
CPC ...... *A61M 5/14546* (2013.01); *A61M 5/1456* (2013.01); *A61M 5/31515* (2013.01)

(58) Field of Classification Search
CPC .... A61M 2005/14573; A61M 5/14546; A61M 5/14566; A61M 5/31515
See application file for complete search history.

(56) References Cited

U.S. PATENT DOCUMENTS 4,931,040 A 6/1990 Haber et al.
5,875,976 A 3/1999 Nelson et al.
(Continued)

FOREIGN PATENT DOCUMENTS

GB 781554 8/1957
GB 2108852 A 5/1983
(Continued)

OTHER PUBLICATIONS

International Search Report mailed Nov. 12, 2019 for the corresponding PCT International Patent Application No. PCT/JP2019/035546.
(Continued)

*Primary Examiner* — Deanna K Hall
(74) *Attorney, Agent, or Firm* — Leason Ellis LLP; Jordan Garner; Mitsuhiro Haraguchi

(57) ABSTRACT

An injection system has: a gasket having a plurality of engaging claws, wherein each of the engaging claws includes an inner surface S1 which defines a hole H having an inlet with an enlarged diameter and an outer surface S2 inclined in a direction away from a perpendicular line P passing through a center of the hole H, and the engaging claws are to be displaced between a widened position and a narrowed position; a rain to be inserted into the hole H so as to engage with the engaging claws; a cylinder, into which the gasket is to be inserted, contacting the outer surfaces S2; and an injection device configured to move the ram forward and injecting a chemical solution in the cylinder. An annular groove which serves as a starting point of deformation of the engaging claws is formed on the gasket.

11 Claims, 11 Drawing Sheets

(56) References Cited

U.S. PATENT DOCUMENTS

| | | | |
|---|---|---|---|
| 5,921,967 A * | 7/1999 | Sadowski | A61M 5/30 604/218 |
| 5,928,202 A | 7/1999 | Linnebjerg | |
| 2010/0130935 A1 | 5/2010 | Hieb et al. | |
| 2014/0081214 A1 | 3/2014 | Hieb et al. | |
| 2016/0243306 A1 | 8/2016 | Hieb et al. | |

FOREIGN PATENT DOCUMENTS

| | | |
|---|---|---|
| JP | 02-011164 A | 1/1990 |
| JP | 2001-507963 A | 6/2001 |
| JP | 2014-111185 A | 6/2014 |
| WO | WO-2018/068957 A1 | 4/2018 |
| WO | WO-2018068957 A1 * | 4/2018 |

OTHER PUBLICATIONS

Extended European Search Report mailed May 17, 2022 for the corresponding European Patent Application No. 19860810.1, 8 pages.

* cited by examiner

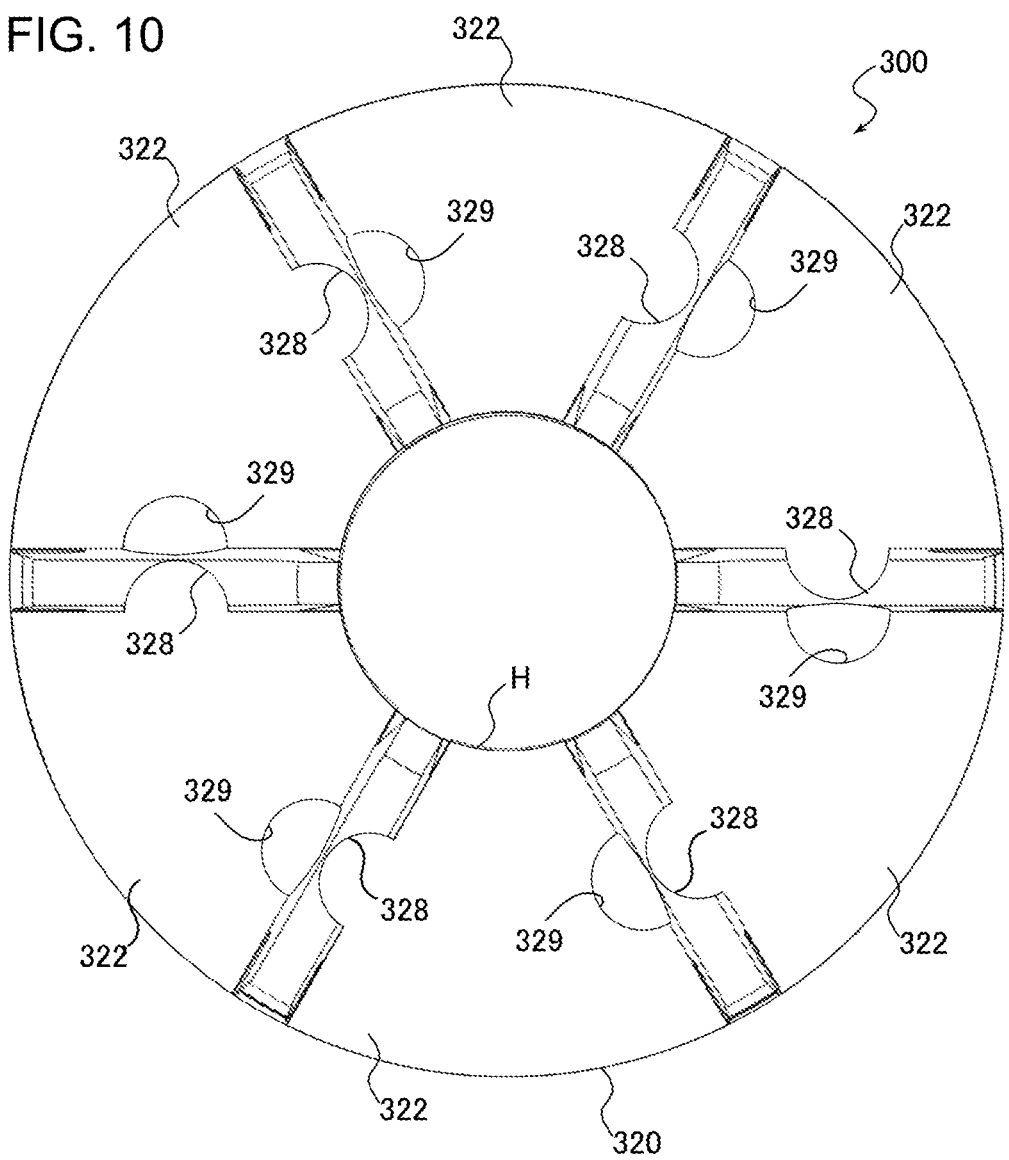

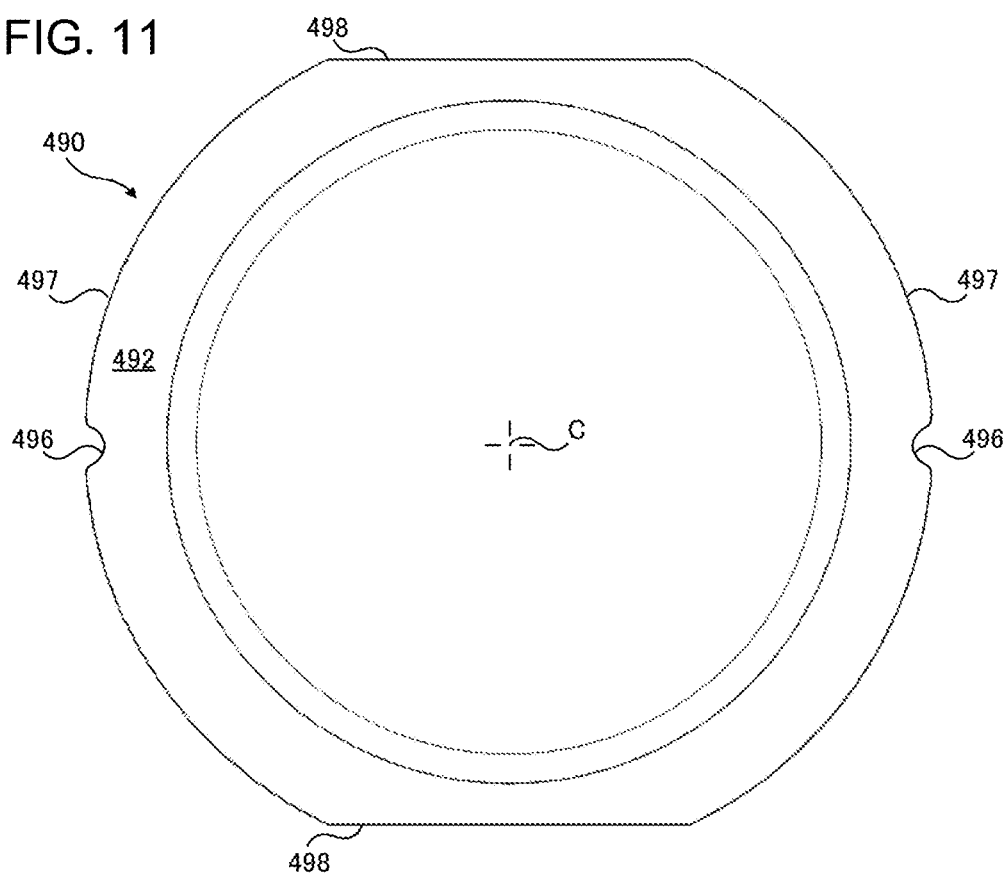

INJECTION SYSTEM, SYRINGE, AND GASKET

CROSS-REFERENCE TO RELATED PATENT APPLICATIONS

This application is a U.S. National Phase Application under 35 U.S.C. § 371 of International Patent Application No. PCT/JP2019/035546 filed on Sep. 10, 2019 and claims the benefit of priority to Japanese Patent Application No. 2018-171532, filed Sep. 13, 2018, all of which are incorporated herein by reference in their entireties. The International Application was published in Japanese on Mar. 19, 2020 as International Publication No. WO/2020/054715 under PCT Article 21(2).

FIELD OF THE INVENTION

The present invention relates to a syringe into which a chemical solution is loaded, a gasket of the syringe, and an injection system on which the syringe is mounted.

BACKGROUND OF THE INVENTION

Conventionally, as a ram and a gasket used in a syringe for injecting a chemical solution, for example, JP2014-111185A describes a plunger having an expandable and shrinkable portion and a syringe having a first inner diameter and a second inner diameter smaller than the first inner diameter. An end of a plunger shaft is inserted into the space of the plunger. When the plunger moves forward in the syringe until it reaches the second inner diameter, the expandable and shrinkable portion shrinks. This causes a tab of the plunger (gasket) to engage with a groove of a plunger shaft (ram).

CITATION LIST

Patent Literature

Patent Literature 1: JP2014-111185A

Technical Problem

In JP2014-111185A, the tab of the gasket engages with the groove of the ram. In order to facilitate the entry of the tab into the groove, the inner dimension of the groove is set larger than the outer dimension of the tab. Also, due to manufacturing tolerances, there may be a gap left between the tab and the groove after the tab has entered the groove. As a result, the ram rattles relative to the gasket and becomes a cause of abnormal sounds. Furthermore, when the center axis of the ram is inclined with respect to the gasket, a pressing force is applied to the syringe in an inclined direction through the gasket. In this case, when a chemical solution is injected at high pressure, there is a possibility that the syringe is detached from an injection device.

SUMMARY OF THE INVENTION

Solution to Problem

In order to overcome the above-described problems, one example of the present invention is an injection system comprising: a gasket having a plurality of engaging claws, wherein each of the engaging claws includes an inner surface which defines a hole having an inlet with an enlarged diameter and an outer surface inclined in a direction away from a perpendicular line passing through a center of the hole, and the engaging claws are to be displaced between a widened position and a narrowed position; a ram to be inserted into the hole so as to engage with the engaging claws; a cylinder, into which the gasket is to be inserted, contacting the outer surfaces of the engaging claws of the inserted gasket; and an injection device configured to move the ram forward and injecting a chemical solution in the cylinder, wherein an annular groove which serves as a starting point of deformation of the engaging claws is formed on the gasket.

Another example of the present invention is a syringe comprising: a gasket having a plurality of engaging claws, wherein each of the engaging claws includes an inner surface which defines a hole having an inlet with an enlarged diameter and an outer surface inclined in a direction away from a perpendicular line passing through a center of the hole, and the engaging claws are to be displaced between a widened position and a narrowed position; and a cylinder, into which the gasket is to be inserted, contacting the outer surfaces of the engaging claws of the inserted gasket, wherein an annular groove which serves as a starting point of deformation of the engaging claws is formed on the gasket.

Still another example of the present invention is a gasket comprising: a plurality of engaging claws, wherein each of the engaging claws includes an inner surface which defines a hole having an inlet with an enlarged diameter and an outer surface inclined in a direction away from a perpendicular line passing through a center of the hole, and the engaging claws are to be displaced between a widened position and a narrowed position, wherein an annular groove which serves as a starting point of deformation of the engaging claws is formed on the gasket.

Further features of the present invention will become apparent from the following description of embodiments illustrated exemplarily with reference to the accompanying drawing.

BRIEF DESCRIPTION OF THE DRAWINGS

FIG. 10 is a schematic rear view of a gasket according to a third embodiment of the present invention.

FIG. 11 is a schematic rear view of a syringe according to a modified embodiment of e present invention.

DETAILED DESCRIPTION OF THE INVENTION

Now, exemplary embodiments for carrying out the present invention will be described in detail with reference to the drawings. It should be noted, however, that dimensions, materials, shapes, and relative positions between components described in the following embodiments are arbitrary and can be changed depending on the configuration or various conditions of the device to which the present invention is applied. Also, unless otherwise mentioned, the scope of the present invention is not limited to the embodiments specifically described below. Incidentally, in the following description, the front side ("front") corresponds to the distal end side of a syringe, and the opposite side corresponds to the rear side ("rear").

EXAMPLE

Figure 1:
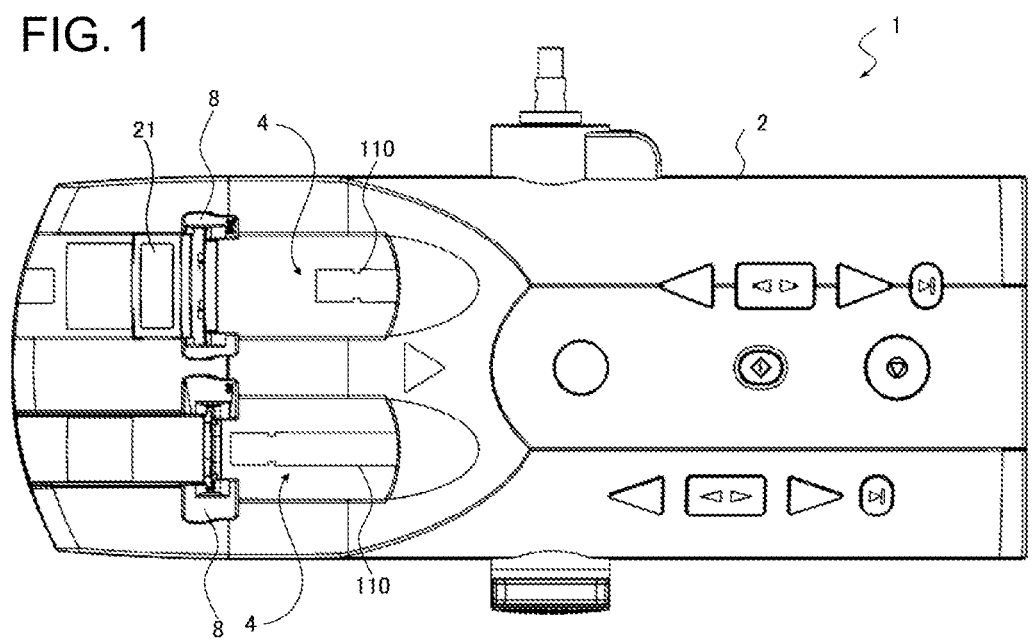
FIG. 1 is a schematic top view of an injection head.
Figure 2:
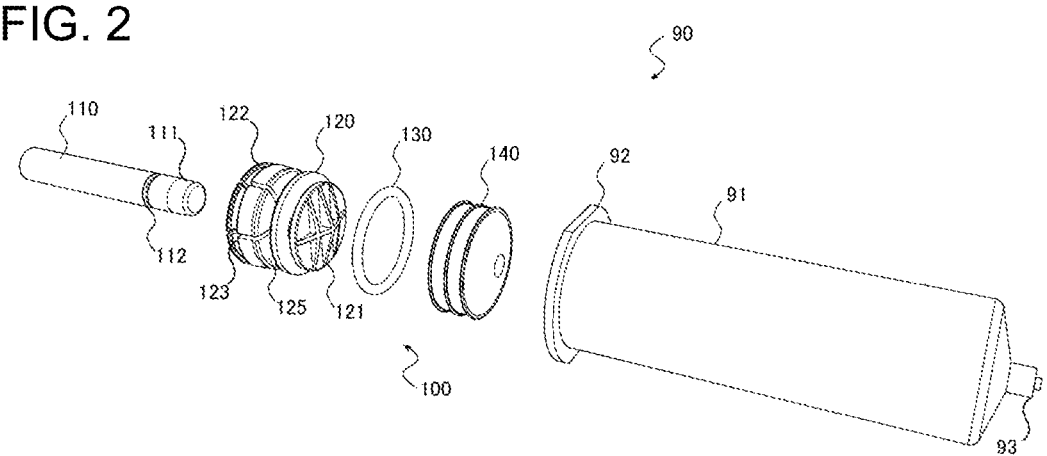
FIG. 2 is a schematic exploded perspective view of a syringe according to a first embodiment of the present invention.

FIG. 1 is a schematic perspective view of an injection system 1 for injecting a chemical solution. As shown in FIG. 1, the injection system 1 is configured to cause rams 110 to move forward, and includes an injection head 2 (injection device) for injecting the chemical solution loaded in a cylinder 91 of a syringe 90 (FIG. 2). Further, the injection system 1 includes adapters 8 for mounting the respective syringes 90 on the injection head 2. The adapters 8 are attached to holders of the injection head 2. The injection head 2 is provided with pressing parts 4 for pushing gaskets 100 (FIG. 2) to be inserted into the respective syringes 90.

Each of the pressing parts 4 is controlled by a control unit (not shown) such that the pressing part 4 presses and moves the gasket 100 forward in the syringe 90 in order to deliver the chemical solution from the syringe 90. Further, the pressing part 4 is provided with a ram 110 which is connected to a drive mechanism (not shown). Specifically, the control unit controls a motor in the injection head 2 such that the ram 110 moves forward when the motor is rotating in a forward direction and the ram 110 moves backward when the motor is rotating in a reverse direction. The injection head 2 also includes a reading unit 21 that reads a data carrier such as an RFID or a bar code provided in the syringe 90 mounted on the associated adapter 8.

Further, the injection system 1 is wired or wirelessly connected to an imaging device (not shown). At the time of injection of the chemical solution and photographing of images, various data are transmitted and received between the imaging device and the injection system 1. The imaging device is, for example, an MRI (Magnetic Resonance Imaging) device, a CT (Computed Tomography) device, an angio imaging device, a PET (Positron Emission Tomography) device, a SPECT (Single Photon Emission Computed Tomography) device, a CT angio device, an MR angio device, an ultrasonic diagnostic device or a vessel imaging device.

Further, the injection system 1 includes a console having a touch panel as a display unit for displaying an injection status of the chemical solution, and a control device (both not shown) having a control unit and a power supply. The console and the injection head 2 can be wired or wirelessly connected to each other. Additionally, a remote controller, such as a hand switch, may be wired or wirelessly connected to the console. The remote controller may also be used to start or stop the injection of the chemical solution. Incidentally, the injection head 2 and the control device can be integrally configured with a caster stand (not shown). Alternatively, the injection head 2 and control device may be provided separately and mounted on the caster stand.

Data of the operation pattern (injection protocol) and data of the chemical solution are stored in the control device in advance. When injecting a chemical solution into a patient, an operator operates the touch panel on the console to enter an injection speed, an injection volume and an injection time, as well as the patient's physical data such as body weight, height, body surface area, heart rate and cardiac output together with the data of the type of chemical solution. Then, the control device calculates an optimum injection condition according to the entered data and the data stored in advance. Thereafter, the control device determines an amount of chemical solution to be injected into the patient and the injection protocol based on the calculated injection condition.

In addition, upon determining die amount of chemical solution and the injection protocol, the control device displays predetermined data or graphs on the touch panel of the console or on a head display of the injection head 2. This allows the operator to see the displayed data or graphs. The data of the operation pattern (injection protocol) and the data of the chemical solution can be entered from an external storage medium.

When injecting the chemical solution, the operator turns on the power of the injection head 2 and mounts the syringe 90 on the injection head 2. Subsequently, the operator presses the injection button displayed on the touch panel. If the injection head 2 is provided with an operation panel, the operator may press an injection button on the operation panel. The operator may press a button on a hand switch to initiate the injection. Alternatively, the operator may turn on the power of the injection head 2 after mounting the syringe 90.

When the injection button is pressed, the control unit sends a forward-rotation signal as a drive voltage to the motor. In response to the forward-rotation signal, the shaft of the motor rotates in a forward direction and the pressing part 4 (ram 110) moves forward. Thereafter, when the injection is completed and the syringe 90 is removed, the control unit sends a reverse-rotation signal as a drive voltage to the motor in order to cause the ram 110 to move backward. In response to the reverse-rotation signal, the shaft of the motor rotates in a reverse direction and the ram 110 moves backward.

Each of the pressing parts 4 has a drive mechanism, which is not shown in the drawings. The drive mechanism includes a transmission mechanism connected to the shaft of the motor, a ball screw shaft connected to the transmission mechanism, a ball screw nut attached to the ball screw shaft, and an actuator connected to the ball screw nut. The transmission mechanism has a pinion gear connected to the shaft and a screw gear connected to the ball screw shaft. The transmission mechanism transmits the rotation from the motor to the ball screw shaft. Therefore, the rotation of the shaft of the motor is transmitted to the ball screw shaft through the pinion gear and the screw gear. Thus, the ball screw shaft rotates in accordance with the transmitted rotation. The ball screw nut slides in the forward direction or the backward direction with the rotation of the ball screw shaft. As the ball screw nut slides, the ram 110 of the pressing part 4 moves forward or backward.

First Embodiment

FIG. 2 is a schematic exploded perspective view of a syringe 90 according to a first embodiment and shows the syringe 90 viewed from the upper front. As shown in FIG. 2, the syringe 90 has a gasket 100 which is slidable in the cylinder 91. The gasket 100 is inserted into the cylinder 91 such that the cylinder 91 contacts an outer surface S2 (FIG. 4) of the inserted gasket 100. Further, the cylinder 91 has a flange 92 which is fitted in a groove of the adapter 8. The gasket 100 includes a sucker 120, an O-ring 130, and a seal member 140.

The sucker 120 has a substantially disc-shaped insertion portion 121, and a plurality of split engaging-claws 122. A plurality of intersecting ribs is formed on the insertion portion 121. Further, an annular groove 125 is formed between the insertion portion 121 and the engaging claws 122. The seal member 140 has annular projections formed on its outer surface. As the annular projections contact the inner surface of the cylinder 91, the cylinder 91 is sealed. Incidentally, in FIG. 2, the three annular projections are formed, but two, one, four or more annular projections may be formed. The seal member 140 has a space formed therein in order to receive the insertion portion 121 and the rear end portion of the seal member 140 protrudes toward the space. Each of the engaging claws 122 has a protrusion 124 (FIG. 3) which engages with an engaging groove 112 formed in the front end portion 111 of the ram 110.

When assembling the gasket 100, firstly, the O-ring 130 is fitted over the insertion portion 121 of the sucker 120 such that the O-ring 130 is eventually received in the groove 123 formed in the engaging claws 122. Then, the insertion portion 121 is inserted into the space in the seal member 140 such that the seal member 140 is attached to the sucker 120. At this time, the rear end portion of the seal member 140 fits in the annular groove formed behind the insertion portion 121. Thus, the seal member 140 is fixed to the sucker 120. The mounted O-ring 130 regulates the engaging claws 122 from spreading. Therefore, it is possible to equalize the gap between each two adjacent engaging claws 122. Consequently, it is possible to equalize the gap between each two adjacent protrusions 124 of the engaging claws 122.

The gasket 100 is assembled in the above-described manner. The sucker 120 is made of an elastic resin such as POM (polyacetal resin), for example, and can be manufactured by molding. The seal member 140 is made of, for example, butyl rubber, and can be manufactured by molding. The ram 110 is, for example, made of stainless steel or aluminum, and can be manufactured by welding a solid and substantially cylindrical front end portion 111 to a hollow pipe. Alternatively, the ram 110 may be manufactured by screwing a solid front end portion 111 into a hollow pipe. Alternatively, a material other than stainless steel or aluminum that is harder than the gasket 100 may be used to manufacture the front end portion 111.

When the motor rotates in a forward direction, with the engaging claws 122 of the gasket 100 being coupled to the front end portion 111 of the ram 110, the pressing part 4 pushes the ram 110 in the forward direction. As the ram 110 and the gasket 100 move forward, the chemical solution in the cylinder 91 is pushed out through the distal end portion 93. As a result, the chemical solution is injected into the patient's body through an extension tube or the like connected to the distal end portion 93. After the injection of the chemical solution, when the motor rotates in the reverse direction, the pressing part 4 pulls the ram 110 in the retracting direction such that the gasket 100 retracts.

As shown in FIG. 2, the corner portion which is continuous with the end face of the front end portion 111 is chamfered. Thus, it is possible to prevent the corner portion from contacting the protrusions 124 at the time of insertion of the ram 110. Incidentally, the corners of the engaging groove 112 of the front end portion 111 are also chamfered so that the corners are rounded. Thus, when the protrusions 124 engage with or disengage from the engaging groove 112, it is possible to suppress a possibility that the protrusions 124 are scraped.

Figure 3:
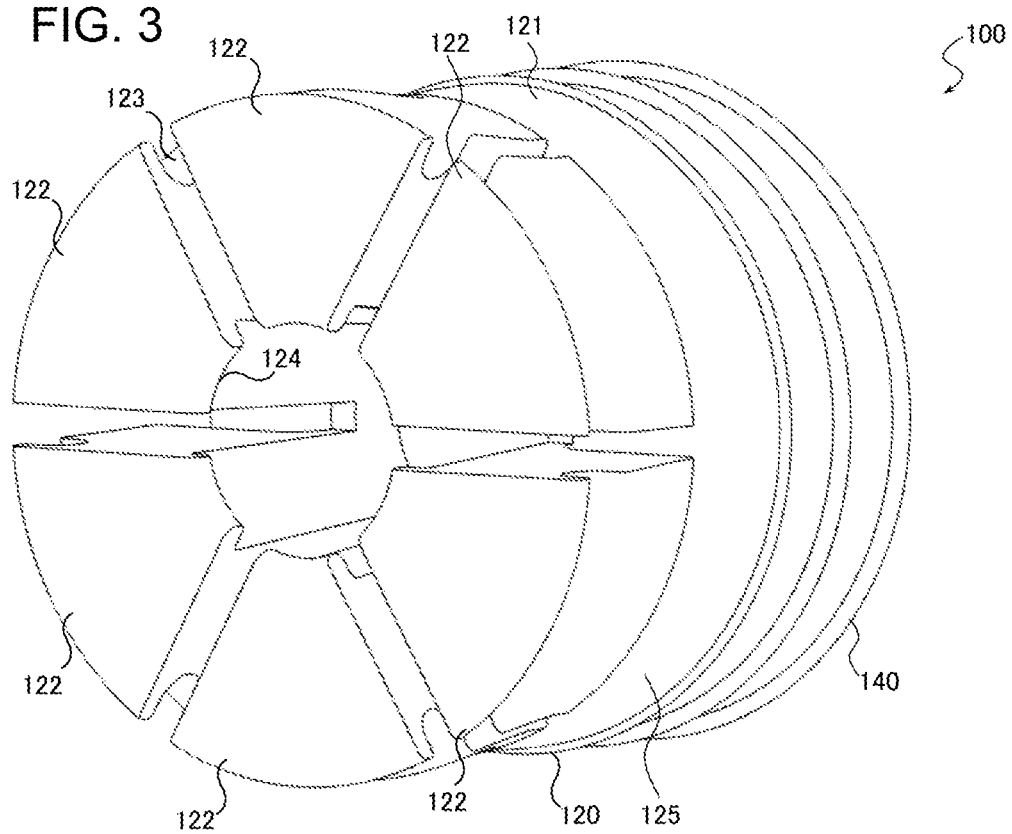
FIG. 3 is a schematic perspective view of a gasket.

FIG. 3 is a schematic perspective view of the gasket 100 as viewed from the rear. For convenience of description, however, the O-ring 130 is omitted. As shown in FIG. 3, the sucker 120 includes the engaging claws 122, each having a substantially fan-shaped cross-sectional shape. The number of the engaging claws 122 may be two or more, and not limited to six. Further, a gap is formed between each two adjacent engaging claws 122. When the gasket 100 is inserted into the cylinder 91, the respective engaging claws 122 are displaced so that each two adjacent engaging claws 122 approach to each other.

Each engaging claw 122 includes the groove 123 in which the O-ring 130 is fitted, and the protrusion 124 for engaging with the engaging groove 112 of the ram 110. The tip of the protrusion 124 is rounded such that the protrusion 124 is easily inserted into the engaging groove 112 of the ram 110. Incidentally, in FIG. 3, reference numerals are given only to the groove 123 and the protrusion 124 of one of the engaging claws 122. However, the groove 123 and the protrusion 124 is provided in each of the six engaging claws 122. All the engaging claws 122 are formed in the same size, and the gap between each two adjacent engaging claws 122 has the same length. Thus, at the time of displacement, it is possible to suppress the positional variations of the respective engaging claws 122 relative to the ram 110. That is, as the gasket 100 is inserted, the respective engaging claws 122 are displaced by the same distance.

The annular groove 125 is formed between the insertion portion 121 and the engaging claws 122 of the sucker 120. The engaging claws 122 are connected to the insertion portion 121 across the portion where the annular groove 125 is formed. To facilitate the displacement (deformation) of the engaging claws 122, the portion where the annular groove 125 is formed is thin as compared to the portion where the protrusion 124 is formed. Further, the sucker 120 has a hole H surrounded by the protrusions 124 (FIG. 4), and the ram 110 is inserted into the hole H such that the ram 110 engages with the engaging claws 122.

Coupling of the Ram 110 and the Gasket 100

Figure 4:
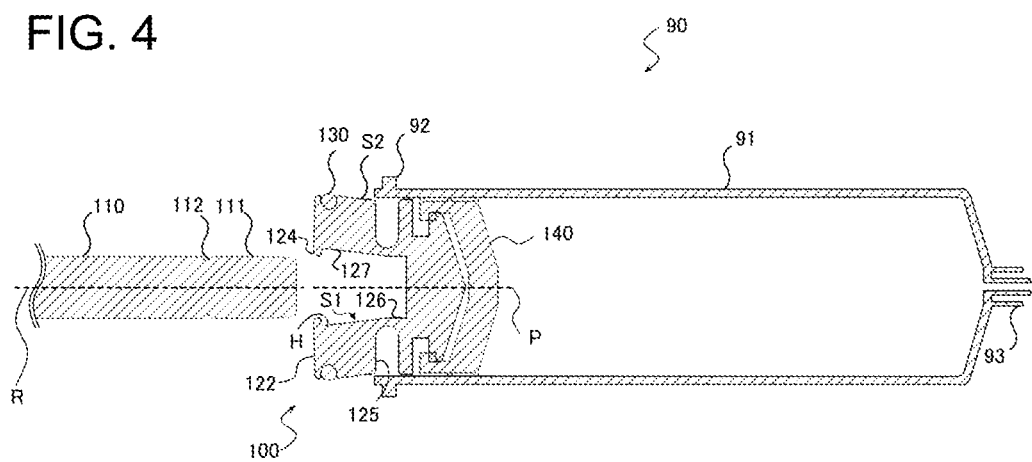
FIG. 4 is a schematic cross-sectional view useful to describe coupling between a ram and the gasket.
Figure 5:
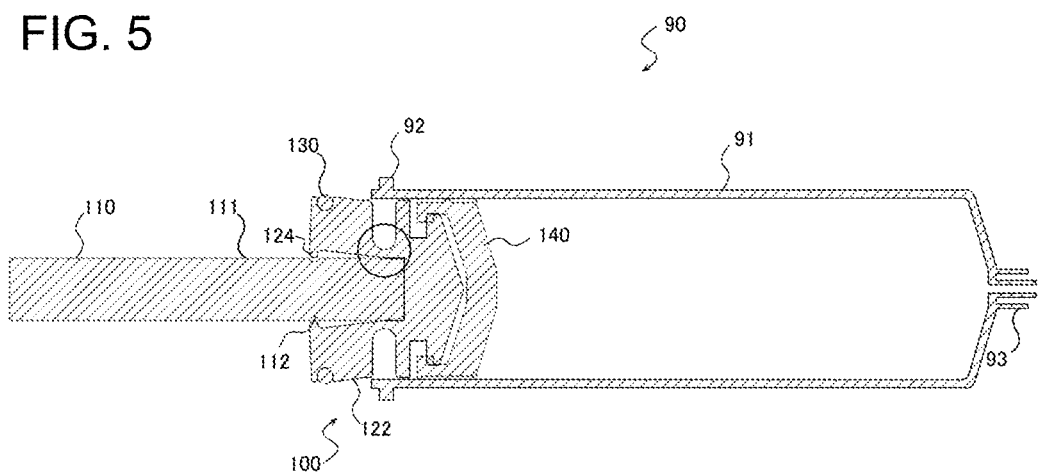
FIG. 5 is another schematic cross-sectional view useful to describe the coupling between the ram and the gasket.
Figure 6:
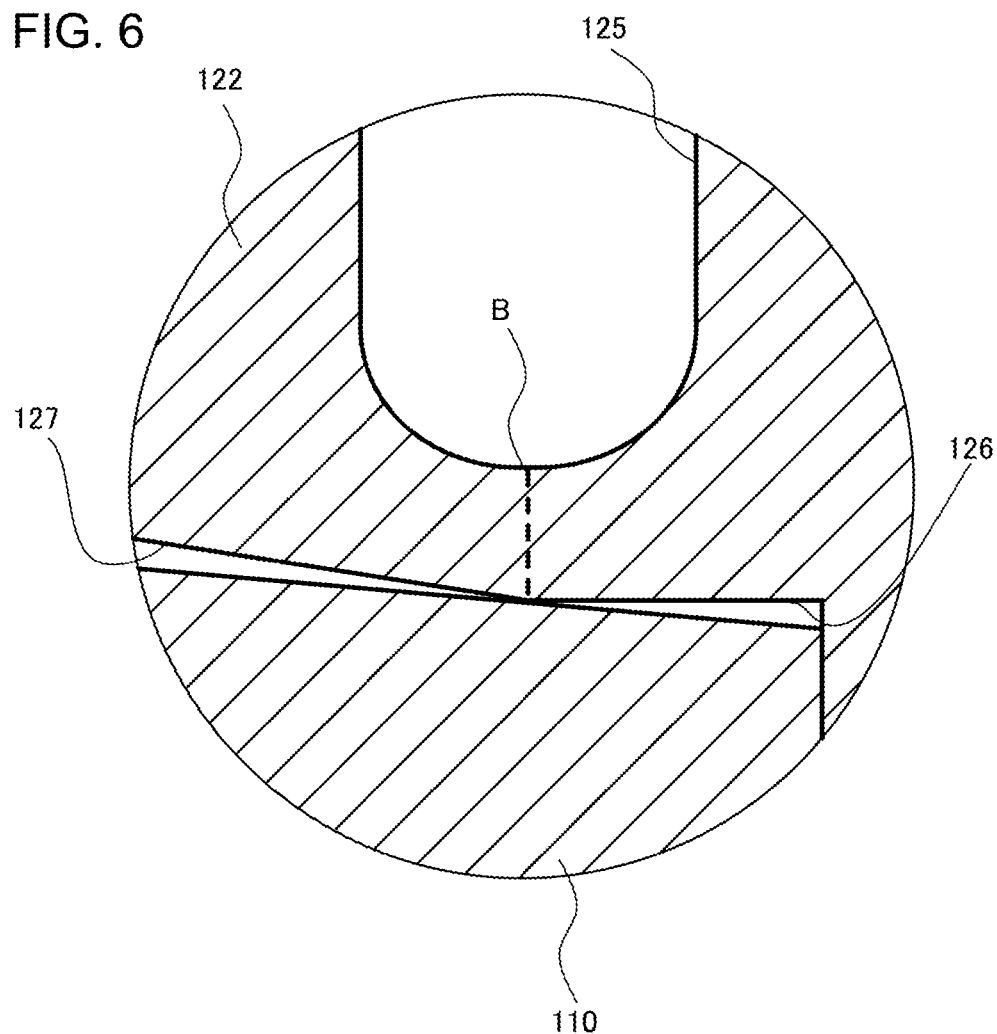
FIG. 6 is a schematic enlarged view of a boundary portion.
Figure 7:
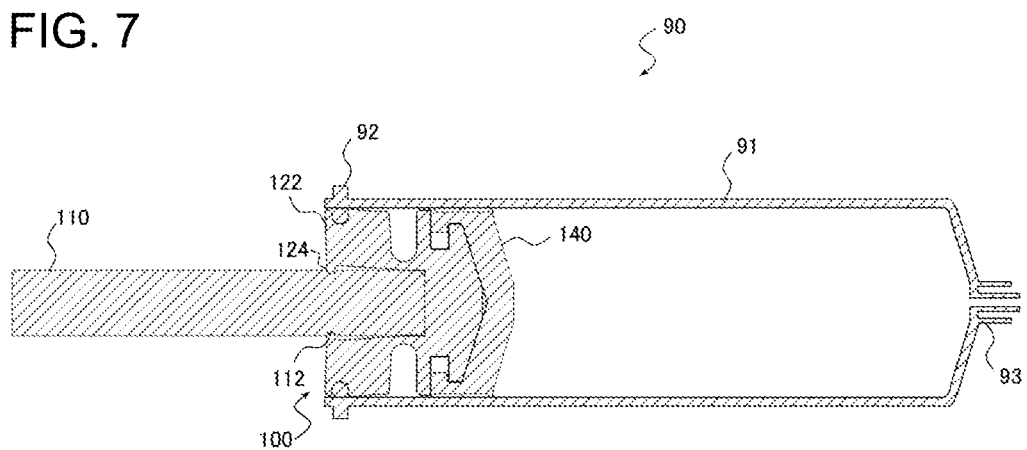
FIG. 7 is a schematic cross-sectional view useful to describe the coupling between the ram and the gasket.
Figure 8:
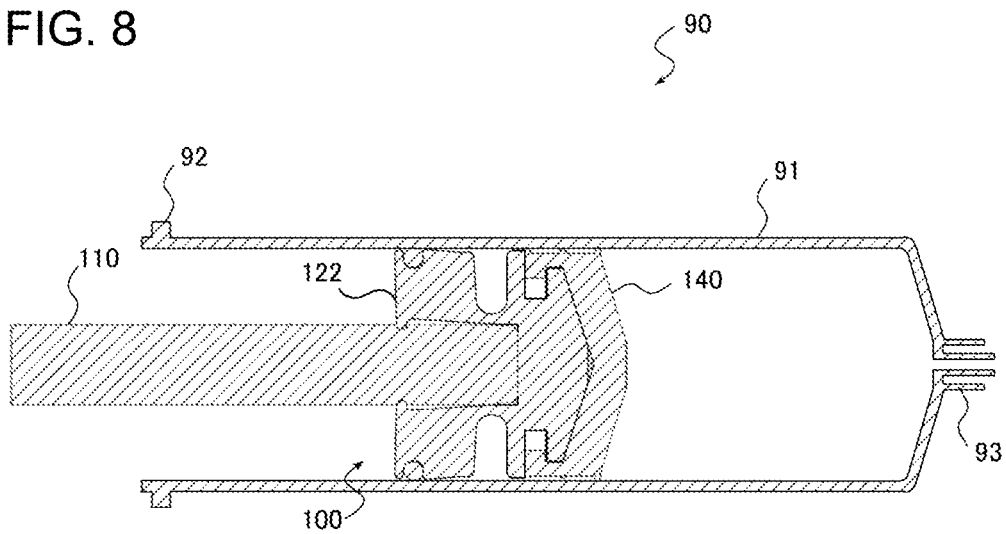
FIG. 8 is another schematic cross-sectional view useful to describe coupling between the ram and the gasket.

Referring to FIG. 4 to FIG. 8, the coupling of the ram 110 and the gasket 100 will be described. FIG. 4 is a schematic cross-sectional view of the syringe 90 prior to inserting the ram 110 into the hole H of the sucker 120. FIG. 5 is a schematic cross-sectional view of the syringe 90 with the rain 110 being inserted into the bore H of the sucker 120. FIG. 6 is a schematic enlarged view of the portion surrounded by the circle in FIG. 5. FIG. 7 is a schematic cross-sectional view of the syringe 90 in which the ram 110 and the gasket 100 are coupled with each other. FIG. 8 is a schematic cross-sectional view of the syringe 90 in which the ram 110 has moved the gasket 100 forward. Each of FIG. 4 to FIG. 8 shows a cross-sectional view along the center axis of the cylinder 91 in the longitudinal direction.

As shown in FIG. 4, the gasket 100 has the hole H whose inlet has an enlarged diameter. That is, the inlet of the hole H into which the ram 110 is inserted has a larger inner diameter as compared to the bottom against which the end face of the ram 110 is pressed. The gasket 100 also has the engaging claws 122 that displace between the open (widened) position (FIG. 5) and the shrunk (narrowed) position (FIG. 7). Each of the engaging claws 122 includes an inner surface S1 including a first inner surface 126 and a second inner surface 127 defining the hole H, and an outer surface S2 inclined in a direction away from a perpendicular line P passing through the center of the hole H (bottom). The first inner surface 126 extends in a ring shape from the bottom of the hole H of the sucker 120, onto which the end face of the front end portion 111 of the ram 110 abuts. Further, the first inner surface 126 extends parallel to the perpendicular line P. The second inner surface 127 extends in a ring shape from the first inner surface 126 to the protrusion 124. When compared to the first inner surface 126, the second inner surface 127 is inclined in a direction away from the perpendicular line P as it approaches the inlet of the hole H.

The outer surface S2 of the engaging claw 122 is inclined away from the perpendicular line P extending in the extending direction of the hole H as the outer surface S2 approaches the inlet of the hole H. Therefore, a length of a line segment, which intersects the perpendicular line P and connects the outer edges of the engaging claws 122, is longer than the length of the inner diameter of the cylinder 91. That is, the outer edges of the engaging claws 122 are situated outside the inner surface of the cylinder 91. Further, each of the engaging claws 122 has the protrusion 124 protruding toward the perpendicular line P. The ram 110 has the annular engaging groove 112 with which the protrusions 124 engage. If the protrusions 124 of the engaging claws 122 displaced to the respective shrunk positions are not aligned in an annular form, the engaging groove 112 may be formed to match positions corresponding to the respective protrusions 124.

In the front end portion 111 of the ram 110, the outer surface of the portion closer to the end face than the engaging groove 112 is also slightly inclined with respect to the center axis R of the ram 110. The inclination angle (1 to 5 degrees as an example) of the outer surface with respect to the center axis R is set to be smaller than the inclination angle (4 to 10 degrees as an example) of the second inner surface 127 with respect to the perpendicular line P. Because the outer surface of the front end portion 111 is inclined, it is possible to guide the front end portion 111 into the hole H such that the center axis R is aligned with the perpendicular line P upon insertion of the front end portion 111.

As shown in FIG. 5, when the ram 110 is inserted into the hole H, the end face of the front end portion 111 abuts against the bottom of the hole H. At this time, the engaging claws 122 are in the open position, and the outer surface of the front end portion 111 abuts against a boundary portion B (FIG. 6) between the first inner surface 126 and the second inner surface 127 of each of the engaging claws 122. That is, the inner dimension of the hole H of the sucker 120 is set so as to abut the outer surface of the front end portion 111 at the boundary portion B. The boundary portion B will be described below with reference to FIG. 6.

As shown in FIG. 6, at a position corresponding to the boundary portion B between the first inner surface 126 and the second inner surface 127 of the gasket 100, formed is the annular groove 125 that serves as a starting point for deformation of each of the engaging claws 122. The annular groove 125 has a substantially semicircular shape in cross section. The boundary portion B is set at a position corresponding to the center of the bottom of the annular groove 125. That is, the center of the bottom of the annular groove 125 and the boundary portion B are situated in the same cross-section perpendicular to the longitudinal direction. As a result, the inner surface S1 of each of the engaging claws 122 is inclined from the boundary portion B. Therefore, at the time of insertion of the front end portion 111, a gap is left between the outer surface of the front end portion 111 and the second inner surface 127. Further, since the outer surface of the front end portion 111 is also slightly inclined, a gap is also left between the outer surface of the front end portion and the first inner surface 126. Incidentally, the annular groove 125 may have a substantially trapezoidal or substantially triangular cross-sectional shape such that the annular groove becomes narrower as it approaches the bottom.

When the ram 110 pushes the gasket 100, the gasket 100 moves forward in the cylinder 91. When the gasket 100 moves forward, the outer surface S2 of each engaging claw 122 abuts against the inner surface of the cylinder 91 since the outer surface S2 of the engaging claw 122 (FIG. 4) is inclined. As the gasket moves forward, the reaction force from the inner surface of the cylinder 91 causes the engaging claw 122 to be displaced toward the perpendicular line P of the sucker 120. At this time, the engaging claw 122 is deformed, with the starting point of the deformation being the center of the bottom of the annular groove 125. Therefore, the boundary portion B is pressed against the front end portion 111.

That is, the boundary portion B is displaced toward the perpendicular line P of the sucker 120. Thus, even if the front end portion 111 is inserted into the hole H toward a position biased with respect to the perpendicular line P, the front end portion 111 is displaced such that the position of the center axis R of the front end portion 111 is aligned with the perpendicular line P. That is, the front end portion 111 is displaced toward the center of the hole H as it is pushed by the boundary portion B. Therefore, it is possible to suppress the inclination of the center axis R with respect to the gasket 100. Furthermore, even if a gap is left between the front end portion 111 and the hole H of the sucker 120 due to manufacturing tolerances or the like, the front end portion 111 is held at the boundary portion B. Thus, it is possible to suppress rattling of the ram 110 relative to the gasket 100.

As shown in FIG. 7, when the gasket 100 is inserted into the cylinder 91, the engaging claws 122 shrink (are narrowed) upon receiving a reaction force from the inner surface of the cylinder 91. Then, the protrusions 124 of the engaging claws 122 in the shrunk positions enter the engaging groove 112, and the protrusions 12.4 engage with the engaging groove 112. Thus, the gasket 100 is coupled to the ram 110. Further, as the engaging claws 122 are displaced, the annular groove 125 is deformed and spreads. Thereafter, as shown in FIG. 8, when the gasket 100 moves forward in the cylinder 91, the seal member 140 presses the chemical solution in the cylinder 91. Thus, the chemical solution is pushed out from the distal end portion 93 and is injected into the body of the patient through an extension tube or the like.

After the injection of the chemical solution, the ram 110 retracts and the gasket 100 which is coupled with the ram 110 also retracts. Then, when the ram 110 and the gasket 100 retract to the position shown in FIG. 5, the restriction by the inner surface of the cylinder 91 is released. Therefore, the engaging claws 122 spread (are widened) outward and the protrusions 124 of the displaced engaging claws 122 move out of the engaging groove 112. Thus, the protrusions 124 disengage from the engaging groove 112. That is, when the ram 110 and the gasket 100 retract until the engaging claws 122 are displaced to the respective open positions, the protrusions 124 disengage from the engaging groove 112. Further, as the engaging claws 122 are displaced, the annular groove 125 narrows such that it returns to the original shape. As the ram 110 further retracts, the gasket 100 remains in the position shown in FIG. 5 due to a frictional force between the seal member 140 and the cylinder 91. Consequently, the ram 110 disengages from the gasket 100 and retracts to the pre-insertion position shown in FIG. 4.

If the ram 110 and the gasket 100 according to the first embodiment are employed, the engaging claws 122 are deformed, with the center of the bottom of the annular groove 125 being the starting point of deformation. Therefore, the engaging claws 122 are evenly displaced toward the perpendicular line P of the sucker 120. Further, the front end portion 111 is held at the boundary portion B. Therefore, the position of the center axis R of the front end portion 111 of the ram 110 is aligned with the perpendicular line P. Thus, when the ram 110 is detached from the gasket 100, it is possible to suppress that the front end portion 111 takes a position biased with respect to the perpendicular line P. Therefore, it is possible to prevent the engaging groove 112 of the front end portion 111 from being caught by the protrusions 124.

Further, if the rain 110 and the gasket 100 according to the first embodiment are employed, it is possible to suppress that the ram 110 rattles relative to the gasket 100 when coupling the gasket 100 and the ram 110 with each other. Furthermore, since the gasket 100 and the ram 110 are directly coupled with each other, it is possible to shorten the distance between the syringe 90 and the pressing part 4. Therefore, the size of the injection head 2 in the injection system 1 can be reduced.

Incidentally, instead of the protrusions 124 and the engaging groove 112, engaging grooves may be formed in the engaging claws 122 of the gasket 100 and an annular projection may be formed on the front end portion 111 of the rain 110. Further, if the engaging claws 122 can be manufactured with high precision, it is possible to omit the O-ring 130.

Second Embodiment

In the first embodiment, the engaging claws 122 of the gasket 100 before insertion protrude outward from the syringe 90. In the second embodiment, a cylinder 291 of a syringe 290 has a skirt portion 295 to cover engaging claws 222. Hereinafter, a second embodiment will be described with reference to FIG. 9, but in the description of the second embodiment, the differences from the first embodiment will be described whereas those components which are already described in the first embodiment are given die same reference numerals and the description thereof will be omitted. Unless otherwise mentioned, the components denoted by the same reference numerals operate and function in the substantially same manner and achieve the substantially same advantages.

Figure 9:
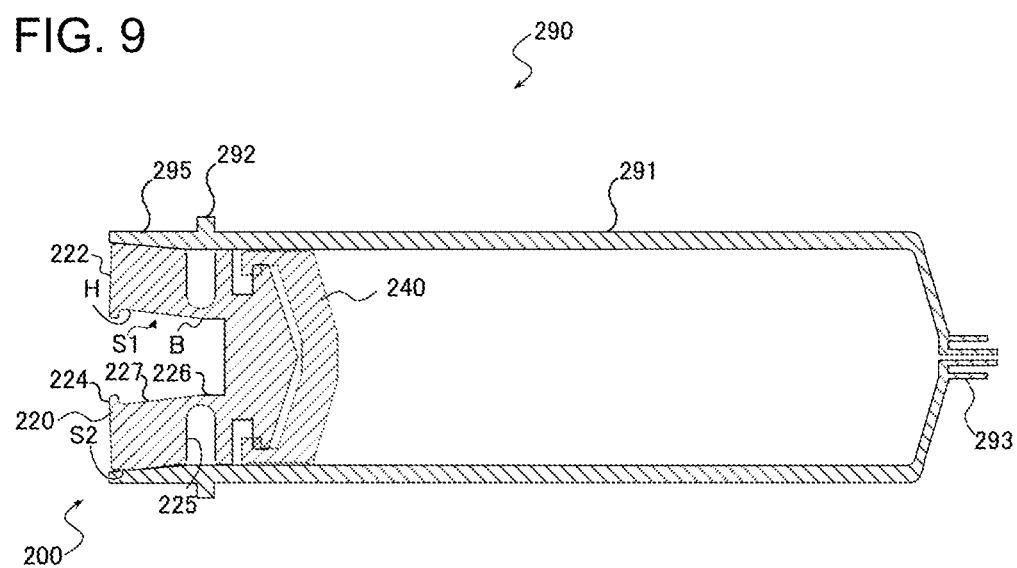
FIG. 9 is a schematic cross-sectional view of a syringe according to a second embodiment of the present invention.

FIG. 9 is a schematic cross-sectional view of the syringe 290 prior to inserting the ram 110 into the hole H of a sucker 220. FIG. 9 shows a cross-sectional view along the longitudinal direction through the center axis of the syringe 290. Since the configuration of the ram 110 is the same as the first embodiment, the ram is not shown in the drawing.

As shown in FIG. 9, the skirt portion 295 is formed on the cylinder 291 of the syringe 290 behind a flange 292. The inner surface of the skirt portion 295 is inclined along the outer surfaces S2 of the engaging claws 222 such that the engaging claws 222 are positioned in the open position. Therefore, the inner dimension of the skirt portion 295 is set to match the outer dimensions of the engaging claws 222 in the open state. That is, the skirt portion 295 has a shape that narrows toward a distal end portion 293. As a result, the engaging claws 222 of the gasket 200 inserted into the inside of the skirt portion 295 are not displaced to the respective shrunk positions. Even when the engaging claws 222 are slightly displaced, the distance between the opposing protrusions 224 maintains a state in which the ram 110 can be inserted. Thus, since the skirt portion 295 covers the engaging claws 222, it is possible to suppress that foreign matters adhere to the engaging claws 222.

Similar to the first embodiment, the gasket 200 of the second embodiment includes the inner surface S1, which has a first inner surface 226 and a second inner surface 227 defining the hole H whose inlet is enlarged, and also includes an annular groove 225 formed at a position corresponding to the boundary portion B between the first inner surface 226 and the second inner surface 227 such that the annular groove 225 becomes a starting point of deformation. On the other hand, the groove 123 is not formed in the engaging claws 222 of the sucker 220 of the gasket 200, and the O-ring 130 is not attached. Instead of the O-ring 130, the skirt portion 295 is used to restrict the spreading of the engaging claws 222. Thus, it is possible to equalize the gap between each two adjacent engaging claws 222 and omit the O-ring 130.

After inserting the front end portion 111 of the ram 110, the gasket 200 moves forward in the cylinder 291 as the ram 110 pushes the gasket 200 through the front end portion 111. As the gasket 200 moves forward, the outer surfaces of the engaging claws 222 pass through the skirt portion 295 and contact the inner surface of the cylinder 291. Along with the forward movement of the gasket, the reaction force from the inner surface of the cylinder 291 causes the engaging claws 222 to be displaced toward the center of the hole H of the sucker 220. At this time, the engaging claws 222 start deforming from the center of the bottom of the annular groove 225.

Then, the boundary portion B between the first inner surface 226 and the second inner surface 227 is pressed against the front end portion 111. When the gasket 200 is further inserted into the cylinder 291, the engaging claws 222 receive a reaction force from the inner surface of the cylinder 291 and shrink. The projections 224 of the engaging claws 222 displaced to the respective shrunk positions enter the engaging groove 112 of the ram 110, and the projections 224 engage with the engaging groove 112. Thus, the gasket 200 is coupled to the ram 110. Thereafter, when the gasket 200 moves forward in the cylinder 291, the seal member 240 presses the chemical solution in the cylinder 291. Thus, the chemical solution is extruded from the distal end portion 293 and is injected into the body of the patient via an extension tube or the like.

After the injection of the chemical solution, the ram 110 retracts and the gasket 200 which is coupled with the ram 110 also retracts. The ram 110 and the gasket 200 retract to a position where the restriction by the inner surface of the cylinder 291 is released. Thus, the engaging claws 222 spread outward and the projections 224 move out of the engaging groove 112. As a result, the projections 224 disengage from the engaging groove 112. As the ram 110 further retracts, the ram 110 disengages from the gasket 200.

When the ram 110 and the gasket 200 according to the above-described second embodiment are employed, the engaging claws 222 are deformed, with the center of the bottom of the annular groove 225 being the starting point of deformation. Therefore, the engaging claws 222 are evenly displaced toward the perpendicular line P of the sucker 220. Further, when coupling the gasket 200 and the ram 110 with each other, it is possible to suppress the rattling of the rain 110 relative to the gasket 200. Furthermore, since the gasket 200 and the ram 110 are directly coupled with each other, it is possible to shorten the distance between the syringe 290 and the pressing part 4. Therefore, the size of the injection head 2 in the injection system 1 can be reduced. Furthermore, when the gasket 200 according to the second embodiment is employed, it is also possible to suppress the adhesion of the foreign matters to the engaging claws 222.

Incidentally, it is also possible to insert the gasket 100 of the first embodiment into the cylinder 291 of the second embodiment.

Third Embodiment

In the third embodiment, each of engaging claws 322 of a gasket 300 has a convex portion 328 and a concave portion 329. Hereinafter, the third embodiment will be described with reference to FIG. 10, but in the description of the third embodiment, the differences from the first embodiment will be described whereas those components which are already described in the first embodiment are given the same reference numerals and the description thereof will be omitted. Unless otherwise mentioned, the components denoted by the same reference numerals operate and function in the substantially same manner and achieve the substantially same advantages.

The convex portion 328 of each of the engaging claws 322 has an outer shape that matches a quarter of a sphere, and is configured to be on the same plane with the engaging claw 322 at the rear end face of a sucker 320 of the gasket 300. Therefore, when viewed from the rear side of the sucker 320, the convex portion 328 has a substantially semicircular shape. The convex portion 328 protrudes toward an adjacent engaging claw 322. The engaging claw 322 has the concave portion 329 for receiving the convex portion 328 of the other adjacent engaging claw 322. The concave portion 329 has a shape complementary to the convex portion 328 and is formed at a position facing the convex portion 328 of the other adjacent engaging claw 322. When viewed from the rear side of the sucker 320, the concave portion 329 also has a substantially semicircular shape and is designed such that the outer dimension of the convex portion 328 matches the inner dimension of the concave portion 329.

After the insertion of the front end portion 111 of the ram 110, the gasket 300 moves forward in the cylinder 91 as the ram 110 pushes the gasket 300 through the front end portion 111. As the gasket 300 moves forward, the reaction force from the inner surface of the cylinder 91 causes the engaging claws 322 to be displaced toward the center of the hole H in the sucker 320. At this time, each of the engaging claws 322 starts deforming from the center of the bottom of the annular groove 125. Furthermore, when the gasket 300 is inserted into the cylinder 91, the engaging claws 322 shrink upon receiving a reaction force from the inner surface of the cylinder 91.

At the same time, each two adjacent engaging claws 322 are displaced so as to approach each other. Therefore, the convex portions 328 are received in the associated concave portions 329 and engaged with the concave portions 329. With the engagement between the convex portions and the concave portions, the distance between the perpendicular line P of the hole H and each engaging claw 322 is made constant, and it is possible to suppress that the inserted ram 110 is biased in the hole H. Thereafter, when the gasket 300 further moves forward in the cylinder 91, the seal member 140 presses the chemical solution in the cylinder 91. Thus, the chemical solution is pushed out from the distal end portion 93 and injected into the body of the patient through an extension tube or the like.

After the injection of the chemical solution, the ram 110 retracts and the gasket 300 which is coupled with the ram 110 also retracts. The ram 110 and the gasket 300 retract to a position where the restriction by the inner surface of the cylinder 91 is released. Thus, the engaging claws 322 spread outward, and the protrusions 124 move out of the engaging groove 112. As a result, the protrusions 124 disengage from the engaging groove 112. As the ram 110 further retracts, the ram 110 disengages from the gasket 300.

When the ram 110 and the gasket 300 according to the above-described third embodiment are employed, it is also possible to suppress the rattling of the ram 110 relative to the gasket 300 when coupling the gasket 300 and the ram 110 with each other. Furthermore, since the gasket 300 and the ram 110 is directly coupled with each other, it is possible to shorten the distance between the syringe 90 and the pressing part 4. Therefore, the size of the injection head 2 in the injection system 1 can be reduced. Furthermore, it is possible to make the distance between the perpendicular line P of the hole H and the engaging claws 322 constant.

Incidentally, the convex portion 328 may have another outer shape. For example, the convex portion 328 may have an outer shape that matches a triangle column or a half of a circular column, which is obtained by dividing the circular column into two equal halves in the length direction of the column. In this configuration, the convex portion 328 extends along the perpendicular line P and the concave portion 329 has a shape complementary to the convex portion 328.

While the present invention has been described with reference to the respective embodiments, the present invention is not limited to the above-described embodiments. Inventions modified to the extent that they are not contrary to the present invention, and inventions equivalent to the present invention are also included in the present invention. Further, each embodiment and modifications described above can be appropriately combined within the scope not contrary to the present invention.

For example, notches or holes may be formed in the engaging claws 122, 222 and 322. With such configuration, the portions where the notches or holes are formed are deformed, and therefore the engaging claws 122, 222 and 322 are easily displaced. Further, the inner surface S1 of the gasket may not be divided into two surfaces. For example, the inner surface S1 may constitute a continuous inclined surface or curved surface. Each of the gaskets 100, 200 and 300 has an outer shape whose cross-section perpendicular to the perpendicular line P is substantially circular. However, any of the gaskets 100, 200 and 300 may have an outer shape whose cross-section perpendicular to the perpendicular line P is substantially elliptical. In such configuration, the seal member 140, 240 and the syringe 90, 290 have an inner shape complementary to the gasket 100, 200, 300.

Further, the syringe 90, 290 into which the chemical solution is loaded may be a prefill syringe. Also, the chemical solution may be manually loaded into the syringe 90, 290 or may be loaded into the syringe 90, 290 by the injection head 2 or a loading device. The syringe 90, 290 may be provided with a data carrier, such as a RFID or bar code. In the data carrier, information about the loaded chemical solution is recorded. The injection system 1 can read the recorded information from the data carrier through the injection head 2 and control the injection amount of the chemical solution. For example, the control device may calculate an optimum injection amount per body weight based on the read information (iodine quantity) of the chemical solution and display it on the touch panel of the console.

Modifications

As shown in FIG. 11, notches 496 may be formed in certain portions of the outer periphery of a flange 492. Specifically, the flange 492 has two arcuate portions 497 to become an arcuate shape with respect to the center axis C of the syringe 490. Furthermore, the flange 492 has two flat portions 498 facing each other between the arcuate portions 497. For example, the flat portions 498 can be formed by cutting certain portions of the flange 492 along straight and parallel lines. The notches 496, which are used for positioning, are formed in the substantially center portions of the respective arcuate portions 497 such that the notches 496 are situated symmetrical with respect to the center axis C. In other words, the notches 496 are formed such that the line segment connecting the two notches 496 is parallel to the flat portions 498. Further, the adapter 8 may be provided with engagement portions for engaging with the notches 496, e.g., locking claws, convex portions or latches.

The syringe 490, which is configured in the above-described manner, is fitted into the adapter 8, with the flange 492 being parallel to the groove of the adapter 8. At this time, the syringe 490 is fitted into the adapter 8 such that the flat portions 498 face the engaging portions of the adapter 8. Subsequently, the syringe 490 is rotated by 90 degrees such that the engagement portions are engaged with the notches 496. Thus, the syringe 490 can be mounted on the adapter 8. As the engagement portions engage with the notches 496, the syringe 490 is positioned relative to the adapter 8 such that the flat portions 498 are horizontal. Thus, the syringe 490 is appropriately held by the adapter 8, and breakage of the syringe 490 can be prevented. Further, since the rattling of the ram 110 is suppressed, it is possible to insert the ram 110 straight into the syringe 490. Accordingly, even when the chemical solution is injected at a high pressure, it is possible to suppress the leakage of the chemical solution from the gasket 100 to the outside of the syringe 490. Alternatively, one, three or more notches 496 may be formed and the notches 496 may be formed in the flat portions 498.

Part or all of the above-described embodiments may be described as in the following supplementary note, but not limited thereto.

Supplementary Note 1

A method of manufacturing a gasket including a sucker having an insertion portion and an engaging claw, and an O-ring and a seal member attached to the sucker, the method comprising:
fitting the O-ring into a groove formed in the engaging claw, and
inserting the insertion portion into the space in the seal member to attach the seal member to the insertion portion.

REFERENCE SYMBOLS LIST

1: Injection system, 2: Injection head, 90: Syringe, 91: Cylinder, 100: Gasket, 110: Ram, 112: Engaging groove, 122: Engaging claw, 124: Protrusion, 125: Annular groove, 126: First inner surface, 127: Second inner surface, 130: O ring, 200: Gasket, 222: Engaging claw, 224: Projection, 225: Annular groove, 295: Skirt, portion, 226: First inner surface, 227: Second inner surface, 290: Syringe, 291: Cylinder, 300: Gasket, 322: Engaging claw, 328: Convex portion, 329: Concave portion, 490: Syringe, B: Boundary portion, H: Hole, P: Perpendicular line, S1: Inner surface, S2: Outer surface

The invention claimed is:

1. An injection system comprising:
a gasket having a plurality of engaging claws, wherein each of the engaging claws includes an inner surface which defines a hole having an inlet with an enlarged diameter and an outer surface, and the engaging claws are to be displaced between a widened position and a narrowed position;
a ram to be inserted into the hole so as to engage with the engaging claws;
a cylinder, into which the gasket is to be inserted, contacting the outer surfaces of the engaging claws of the inserted gasket; and
an injection device configured to move the ram forward and injecting a chemical solution in the cylinder, wherein
a groove which serves as a starting point of deformation of the engaging claws is formed on the gasket,
the inner surface includes a first inner surface which extends along a perpendicular line perpendicular to a radial direction of the gasket, and a second inner surface which is inclined in a direction away from the perpendicular line, and
the groove is formed at a position corresponding to a boundary portion between the first inner surface and the second inner surface.

2. The injection system according to claim 1, wherein the engaging claw has a protrusion protruding toward the perpendicular line passing through a center of the hole, and
the ram has an engaging groove with which the protrusion engages.

3. The injection system according to claim 1, wherein the first inner surface extends parallel to the perpendicular line.

4. The injection system according to claim 1, wherein the cylinder has a skirt portion to cover the engaging claws.

5. The injection system according to claim 4, wherein an inner surface of the skirt portion is inclined along the outer surface so that the engaging claw is positioned in the widened position.

6. The injection system according to claim 1, wherein the engaging claw has a convex portion protruding toward an adjacent engaging claw, and a concave portion receiving another convex portion of another adjacent engaging claw.

7. The injection system according to claim 1, wherein the groove is an annular groove formed on the gasket.

8. The injection system according to claim 1, wherein the outer surface is inclined in a direction away from the perpendicular line passing through a center of the hole.

9. A injection system comprising:
a gasket having a plurality of engaging claws, wherein each of the engaging claws includes an inner surface which defines a hole having an inlet with an enlarged diameter and an outer surface, and the engaging claws are to be displaced between a widened position and a narrowed position;
a ram to be inserted into the hole so as to engage with the engaging claws;
a cylinder, into which the gasket is to be inserted, contacting the outer surfaces of the engaging claws of the inserted gasket; and
an injection device configured to move the ram forward and injecting a chemical solution in the cylinder, wherein
a groove which serves as a starting point of deformation of the engaging claws is formed on the gasket, and the gasket has an O-ring fitted into a groove formed on the engaging claw.

10. A syringe comprising:

a gasket having a plurality of engaging claws, wherein each of the engaging claws includes an inner surface which defines a hole having an inlet with an enlarged diameter and an outer surface, and the engaging claws are to be displaced between a widened position and a narrowed position; and a cylinder, into which the gasket is to be inserted, contacting the outer surfaces of the engaging claws of the inserted gasket, wherein a groove which serves as a starting point of deformation of the engaging claws is formed on the gasket, the inner surface includes a first inner surface which extends along a perpendicular line perpendicular to a radial direction of the gasket, and a second inner surface which is inclined in a direction away from the perpendicular line, and the groove is formed at a position corresponding to a boundary portion between the first inner surface and the second inner surface.

11. A gasket comprising:

a plurality of engaging claws, wherein each of the engaging claws includes an inner surface which defines a hole having an inlet with an enlarged diameter and an outer surface, and the engaging claws are to be displaced between a widened position and a narrowed position, wherein a groove which serves as a starting point of deformation of the engaging claws is formed on the gasket, the inner surface includes a first inner surface which extends along a perpendicular line perpendicular to a radial direction of the gasket, and a second inner surface which is inclined in a direction away from the perpendicular line, and the groove is formed at a position corresponding to a boundary portion between the first inner surface and the second inner surface.

\* \* \* \* \*